(12) United States Patent  (10) Patent No.: US 7,834,991 B2
Schwarz et al.  (45) Date of Patent: Nov. 16, 2010

(54) DETERMINING SURFACE PROPERTIES WITH ANGLE OFFSET CORRECTION

(75) Inventors: Peter Schwarz, Koenigsdorf (DE); Konrad Lex, Koenigsdorf (DE)

(73) Assignee: BYK Gardner GmbH (DE)

( * ) Notice: Subject to any disclaimer, the term of this patent is extended or adjusted under 35 U.S.C. 154(b) by 135 days.

(21) Appl. No.: 11/774,376

(22) Filed: Jul. 6, 2007

(65) Prior Publication Data
US 2008/0013075 A1    Jan. 17, 2008

(30) Foreign Application Priority Data
Jul. 13, 2006 (DE) ................. 10 2006 032 404
Jul. 13, 2006 (DE) ................. 10 2006 032 405

(51) Int. Cl.
*G01N 21/00* (2006.01)
(52) U.S. Cl. ................. 356/237.1; 356/237.2
(58) Field of Classification Search ... 356/237.1–237.6, 356/326, 364, 369, 370, 445–448; 250/225, 250/559.11, 559.49, 574
See application file for complete search history.

(56) References Cited

U.S. PATENT DOCUMENTS

| 4,253,768 | A | * | 3/1981 | Yaroshuk et al. ............. 356/431 |
| 4,957,368 | A | * | 9/1990 | Smith ......................... 356/369 |
| 6,166,393 | A |   | 12/2000 | Paul et al. ............... 250/559.08 |
| 7,433,055 | B2 |  | 10/2008 | Schwarz et al. ............. 356/600 |
| 7,626,709 | B2 |  | 12/2009 | Schwarz et al. ............. 356/600 |
| 2001/0015414 | A1 | * | 8/2001 | Keranen et al. ........ 250/559.45 |

FOREIGN PATENT DOCUMENTS

| JP | 61-54429 | 3/1986 |
| JP | 61-61042 | 3/1986 |
| JP | 1-257250 | 10/1989 |
| JP | 3-51723 | 3/1991 |
| JP | 4-20845 | 1/1992 |
| JP | 10-246616 | 9/1998 |
| JP | 11-39651 | 2/1999 |
| JP | 2001-242091 | 9/2001 |
| JP | 2001-514386 | 9/2001 |
| JP | 2005-326389 | 11/2005 |
| JP | 2006-30203 | 2/2006 |

OTHER PUBLICATIONS

Japanese Official Action, dated May 12, 2009, (3 pgs).
JP OA Translation, Jan. 9, 2009, (7 pages).

* cited by examiner

*Primary Examiner*—Gregory J Toatley, Jr.
*Assistant Examiner*—Tri T Ton
(74) *Attorney, Agent, or Firm*—Hayes Soloway P.C.

(57) ABSTRACT

An apparatus for determining surface properties, comprises at least a first radiation device which emits radiation onto a surface to be analyzed, at least a first radiation detector device which receives at least part of the radiation emitted by the at least one radiation device and then scattered or reflected by the surface and outputs at least a first measurement signal which is characteristic of the reflected or scattered radiation, and at least a further radiation detector device which receives at least part of the radiation emitted by the at least one radiation device and then scattered or reflected by a surface and outputs at least a second measurement signal which is characteristic of the reflected or scattered radiation.

14 Claims, 3 Drawing Sheets

DETERMINING SURFACE PROPERTIES WITH ANGLE OFFSET CORRECTION

FIELD OF THE INVENTION

The present invention relates to a method and an apparatus for determining surface properties such as, in particular but not exclusively, the colour, orange peel or similar properties of a surface to be analysed.

The invention will be described with reference to surfaces of motor vehicles. However, it is pointed out that the invention can also be used on other surfaces, such as for example the coatings of furniture, of floor coverings and the like.

BACKGROUND OF THE INVENTION

The optical impression of objects or of the surfaces thereof, particularly surfaces on motor vehicles, is greatly determined by the surface properties thereof. Since the human eye is suitable only to a limited extent for the objective determination of surface properties, there is a need for aids and apparatuses for the qualitative and quantitative determination of surface properties.

Surface properties such as, for example, gloss, orange peel, colour, macrostructure or microstructure, image sharpness, haze, surface structure and/or surface topography and the like are determined.

The prior art discloses apparatuses in which a radiation device emits radiation onto the surface to be analyzed and the radiation reflected and/or scattered by this surface is received by a detector and evaluated. These apparatuses operate satisfactorily and allow objective classification of the surface in question.

However, during the measurement the problem arises that the tilt of the apparatus with respect to the surface for example as a result of curvatures of the surface is not constant, but varies. Especially changes of tilt with respect to the surface in the direction of movement may have dramatical impact on the result of measurement. So even changes of angles by a fraction of degree can seriously falsify the measurement.

It is therefore the object of the present invention to provide an apparatus and a method taking into consideration influences which arise from changes of tilt of the apparatus with respect to the surface. Beside, an apparatus should be provided allowing for a differentiation of such effects which evoke form a change inclination and such effects that are, on the other hand, due to changes in surface condition. Finally, statements shall be enabled regarding the physical causes of changes of radiation reaching the detector devices.

SUMMARY OF THE INVENTION

The apparatus according to the invention for determining surface properties comprises at least a first radiation device which emits radiation onto a surface to be analyzed. Beside, at least a first radiation detector device is provided which receives at least part of the radiation emitted by the at least one radiation device and then scattered and/or reflected by the surface and outputs at least first measurement signal which is characteristic of the reflected and/or scattered radiation.

Furthermore at least one second radiation detector device is provided which receives at least part of the radiation emitted by the at least one radiation device and then scattered and/or reflected by the surface and outputs at least a second measurement signal which is characteristic of the reflected and/or scattered radiation.

According to one aspect of the invention, the first radiation detector device is offset by a first predefined angle and the second radiation detector device is offset by a second predefined angle with respect to the direction of the radiation reflected by the surface and the first and second predefined angle are essentially equal and opposite to one another with respect to the direction of the radiation reflected by the surface.

Radiation is understood to mean any type of radiation, such as for example infrared light, ultraviolet light, infrared light, light in the visible wavelength range, X-ray radiation and the like. The radiation used is preferably light in the visible range and particularly preferably a standardised white light.

A property characteristic of the radiation is understood to mean, in particular but not exclusively, the intensity thereof, the spectral range or wavelength thereof, the polarization thereof or a combination of these properties.

According to the invention, the two radiation detector devices are thus arranged essentially the same distance away from the direction of the reflected radiation. Preferably, both the radiation device and the radiation detector devices are arranged in the same plane, so that the observed beam paths also run essentially in one plane, which is particularly preferably perpendicular to the surface to be analysed.

In the case of an exactly perpendicular orientation of the apparatus with respect to the surface, it is to be expected that the two radiation detector devices receive essentially the same radiation intensity since they are located essentially the same distance away from the expected maximum of the radiation at the reflection angle. The intensity distribution reaches a maximum at the respective reflection angle and then decreases for example in a Lorenz or Gaussian form towards the flanks. If tilting of the apparatus with respect to the surface occurs in the plane of the beam paths, for example due to curvatures, the angle of the reflected light will also change. It is thus possible for example that the reflected light is reflected by the surface in a direction which is closer to the first radiation detector device and further away from the second radiation detector device. In this case, the first radiation detector device will detect a higher intensity than the second radiation detector device. The tilt angle of the apparatus with respect to the surface can be deduced from a relationship between the measured intensities, and a measurement result can be corrected on the basis of this deduction.

If, on the other hand, the condition of the surface changes, for example the layer thickness thereof, then possibly the intensity of the reflected light will change but not the direction thereof. Here, the intensity detected by the two radiation detector devices will thus change in the same way. The observer can deduce therefrom that there is no tilting of the apparatus with respect to the surface.

An essentially equal but opposite angle is understood to mean that the two angles of the radiation detector devices have essentially the same value with respect to the direction of the reflected light, with tolerances of up to 3° also being possible. In a further embodiment, it would also be possible to arrange the radiation detector devices at different angles with respect to the direction of the reflected light, and to take this into account accordingly when evaluating the intensity ratios.

A processor device is preferably provided which, from a relationship between the first measurement signal and the second measurement signal, takes account of the orientation of the apparatus with respect to the surface. For example, a straight orientation of the apparatus can be deduced from identical intensities or an intensity difference of 0. This intensity difference of 0 occurs in particular when the two radiation detector devices are arranged at equal and opposite angles with respect to the direction of the reflected light. If the angles do not exactly correspond to one another, this must accordingly be taken into account by the processor device. In this case, the intensity distribution of the reflected light will particularly preferably also be taken into account.

By providing further radiation detector devices for example outside the above-mentioned plane of the beam paths, corresponding measurements also for tilting of the apparatus perpendicular to the abovementioned plane are possible, and it is thus possible overall to record the precise tilting of the apparatus in three-dimensional space with respect to the surface.

Preferably, the relationship between the first measurement signal and the second measurement signal, respectively the resulting values from those measurements signals, is the difference or the ratio of these values. However, further mathematical variables such as the product might be consulted.

Preferably, the predefined angles have a value between 5° and 35°, preferably between 10° and 30°, preferably between 15° and 25°, more preferably at 15°. The particular angles, on one hand, should not be to far a part to allow for reception of parts of the reflected light. On the other hand, the angles should not be selected to be too small to obtain a separation of both flanks of the reflected light intensity.

In a further preferred embodiment, the radiation device emits the radiation at a predefined emission angle $\alpha 1$ onto the surface, and this angle is between 5° and 45°, preferably between 10° an 35°, more preferably between 10° and 25° and particularly preferably in the region of 15° with respect to a direction perpendicular to the surface.

When selecting this angle, care must be taken in particular to ensure that it is not selected to be too large, since if the angle is too large there is a very large offset of the reflected radiation due to unevenesses. In addition, the colour measurement is made more difficult if the angles are too large. On the other hand this angle should also not be too small, in order to ensure that the angle between the emitted and the reflected radiation is large enough to be able to arrange radiation detector devices therebetween.

In a further preferred embodiment, an absorption device is provided which absorbs the radiation reflected by the surface. This absorption device is thus preferably arranged at the reflection angle with respect to the emitted radiation. Preferably, the absorption device is arranged in such a way that it also covers predefined angle ranges of for example 2° to 10° degrees around the reflection angle. The absorption device may in this case be designed as a radiation-absorbing tube or the like. By providing this absorption device, undesired effects due to scattered light are reduced.

In a further preferred embodiment, a further radiation detector device is provided which receives at least part of the radiation emitted by the at least one radiation device and then scattered and/or reflected by the surface and outputs at least a second measurement signal which is characteristic of the reflected and/or scattered radiation. This further radiation detection device can be used, for example, to determine effects in colour change of surfaces. This further radiation detector device is preferably arranged in a large angle distance with respect to the direction of reflected radiation. Thus it is prevented, that reflected radiation reaches in direction of the further radiation device.

The further radiation detector device is preferably arranged in an angle with respect to the direction perpendicular to the surface, this angle having a value between 30° and 60° and preferably of a approximately 45° Preferably, the radiation device and the further detector device are located at the same side with respect to the direction perpendicular to the surface. In this case the further detector device, on one hand, and the first and second detector devices on the other hand are located on different sides with respect to the perpendicular direction.

A processor device is preferably provided which compares the further measurement signal with at least the first or the second measurement signal which outputs a characteristic value for this comparison. It is thereby for example possible, to sum up or to respectively compare percentual relations of intensity values of the first and the further detector device. By these arrangements certain categories of colour unevenness on the surface can be differentiated, as for example such surface changes which are caused by a difference in layer thickness, change the signals of the first and the further radiation detector devices in the same direction and, on the other hand, such colour unevenness which results from a certain orientation of colour pigments, changes or influences the signals in a different direction. This will be illustrated in more detail in reference to the figures. Preferably, a processor device is provided that compares the further measurement signal with at least the first or the second measurement signal and outputs a characteristic value for this comparison.

The present invention is further directed on an apparatus for determining characteristic properties with at least a first radiation device which emits radiation onto a surface to be analysed, at least a first radiation detector device which receives at least part of the radiation emitted by the at least one radiation device and than scattered and/or reflected by the surface and outputs at least the first measurement signal which is characteristic of the reflected and/or scattered radiation.

In addition, at least one further radiation detector device is provided which receives at least part of the radiation emitted by the at least one radiation device and than scattered and/or reflected by the surface and outputs at least a second measurement signal which is characteristic of the reflected and/or scattered radiation. According to the invention, the first radiation detector device is offset by a first predefined angle with respect to the direction of the radiation reflected by this surface, the further radiation detector device is offset by a further predefined angle with respect to the direction of the radiation reflected by the surface and a processor device is provided that determines a value characteristic for surface condition from a relation between the first measurement signal and the further measurement signal.

In this embodiment according to the invention, the two angles under which the first and the further radiation detector device are arranged, are not necessarily essentially symmetric with respect to the direction of the reflected radiation but preferably asymmetric to this. The apparatus according to the invention provides to also differentiate those effects which are caused by different kinds of surface unevenness and which can not be differentiated by a radiation detector device. More precisely, such effects which are caused by changing layer thickness and thereby associated concentration changes of colour pigments, and such effects that are caused by an uneven arrangement of effect pigments, are distinguished from one another. This will be illustrated in more detail with reference to the figures.

In a further preferred embodiment, an intensity measuring device is provided which measures the intensity of the radiation emitted by the radiation device before said radiation impinges on the surface. If for example a white LED is used as the radiation device or radiation source, the intensity thereof is not exactly constant over time. For instance, changes in the intensity may be caused for example due to heating of the radiation source. Since the intensities determined in each case by the radiation detector device are also relevant for determining surface properties, the intensity measuring devices serves to carry out a calibration of the respectively determined intensities. This is particularly beneficial in the pulsed mode.

Preferably, at least a first radiation device has at least one radiation source selected from a group of radiation sources including thermal radiation sources, such as in particular but not exclusively incandescent lamps, halogen lamps, coherent and non-coherent semiconductor radiation sources, such as in particular but not exclusively LEDs, gas discharge radiation sources, lasers, combinations thereof and the like. The radiation source used is particularly preferably an LED which emits white light.

In a further preferred embodiment, a layer thickness measuring device is provided. The respective layer thickness can thus be determined for example inductively. In a further preferred embodiment, the apparatus comprises a movement device for moving the apparatus with respect to the surface along a predefined, preferably essentially rectilinear movement direction. This movement device may comprise wheels for example, wherein particularly preferably at least one wheel is coupled to a distance measuring device.

It is thus possible to record a profile of a surface to be analyzed.

In a further preferred embodiment, at least one radiation detector device allows locally resolved reception of the radiation impinging thereon. In this case, the radiation detector device may have a CCD chip or the like. In this way, it is possible not just to determine intensities of the impinging radiation but also to display a differentiated image of the surface.

The present invention also relates to a method for determining surface properties, wherein in a first method step radiation is emitted onto a surface to be analyzed. In a further method step, at least part of the radiation emitted onto the surface and reflected by the latter is detected by means of a first radiation detector device and a first signal characteristic of this reflected radiation is output. Furthermore, at least part of the radiation emitted onto the surface and reflected by the latter is detected by means of a second radiation detector device and a second signal characteristic of this reflected radiation is output. In a further method step, the first signal is compared with the second signal and, based on this comparison, a geometric position of the radiation device with respect to the surface is taken into account. More specifically, preferably a tilting or the angle of inclination of the apparatus with respect to the surface in the plane of the radiation devices is determined by comparing the first and second signal.

Preferably, at least one signal is corrected by taking account of the geometrical position of the radiation device with respect to the surface. This may be for example a signal which was determined by the radiation detector device for the surface, and the correction accordingly takes place by taking account of any tilting.

Preferably, the first radiation detector device is offset by a first predefined angle with respect to the direction of the radiation reflected by the surface and the second radiation detector device is offset by a second predefined angle with respect to the direction of the radiation reflected by the surface, wherein the angles are essentially equal and opposite to one another with respect to the direction of the radiation reflected by the surface.

Preferably, an apparatus of the type described above is used to carry out the method according to the invention.

The present invention also relates to a method for determining surface properties, wherein in a first method step radiation is emitted onto a surface to be analyzed, and in a further method step at least part of the radiation emitted onto the surface and reflected by the latter is detected by means of a first radiation detector device and a first signal characteristic of this reflected radiation is output.

As an alternative or in addition, a certain type of colour change or the cause thereof is identified by comparing the first signal and the second signal or the first signal and a further signal which originates from a further radiation detector device. Colour changes are generally caused by those states of the surface which differ from an ideal surface, i.e. a surface which in particular has no concentration fluctuations of the colour pigments due to changes in layer thickness and no incorrect orientations of effect pigments (e.g. aluminium flakes). In particular, by means of the method according to the invention, changes in the colour pigment concentration can be distinguished from those effects caused by an incorrect orientation of effect pigments. More specifically, based on the value characteristic of the comparison, it is possible to distinguish between signal changes caused by a change in layer thickness and signal changes caused by an incorrect arrangement of pigments.

Preferably, the first signal and the further signal are output in each case in two different areas of the surface and at lest one surface property is determined from a comparison of the first and further signals. By comparing the first and further signals, it is possible to check whether the two signals change in one specific direction or in opposite directions. As described above, this can in turn be used to deduce the physical causes of colour changes.

BRIEF DESCRIPTION OF THE DRAWINGS

Further advantages and embodiments will emerge from the appended drawings, in which.

DETAILED DESCRIPTION OF THE DRAWINGS

Figure 1:
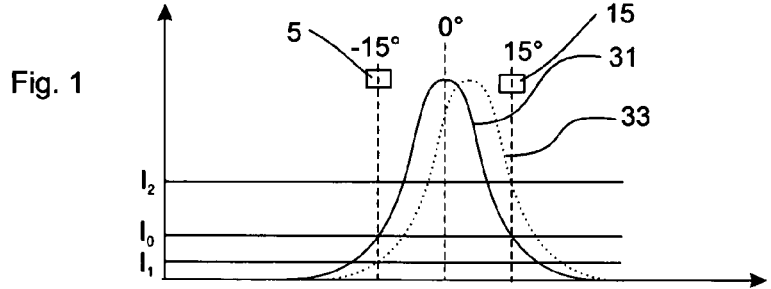
FIG. 1 shows a diagram to illustrate a first problem on which the invention is based.

FIG. 1 shows an intensity distribution of radiation emitted onto a surface and reflected by the latter. Here, the dashed line bearing the marking 0° denotes the reflection angle. For the sake of simplification, the respective angles and the lines thereof have been plotted on a straight line.

If the apparatus is not tilted with respect to the surface, the intensity curve 31 is to be expected. In this case, the two radiation detector devices 5 and 15, which are arranged at −15° and 15°, in each case receive the same intensity $I_0$. However, if the apparatus is tilted with respect to the surface, the intensity distribution or the signal is shifted, as shown for example by the dotted line 33. In this case, the radiation detector device arranged at +15° will receive a higher intensity $I_2$ and the radiation detector device arranged at −15° will receive a corresponding lower intensity $I_1$. The tilting can be taken into account from the ratio between the intensity values $I_1$ and $I_2$. Particularly preferably, the two radiation detector devices are arranged in such a way that intensity $I_0$ is located in that region of the intensity distribution in which an approximately linear intensity profile with respect to the angle is to be expected. In the case of tilting, the differences between $I_1$ and $I_0$ and between $I_2$ and $I_0$ are then approximately the same.

Figure 2A:
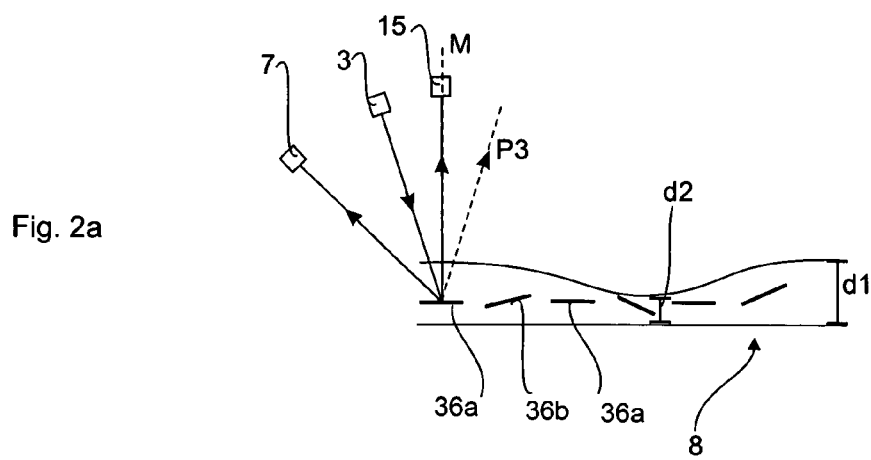
FIGS. 2a-2c show schematic diagrams to illustrate a second problem on which the invention is based.
Figure 2B:
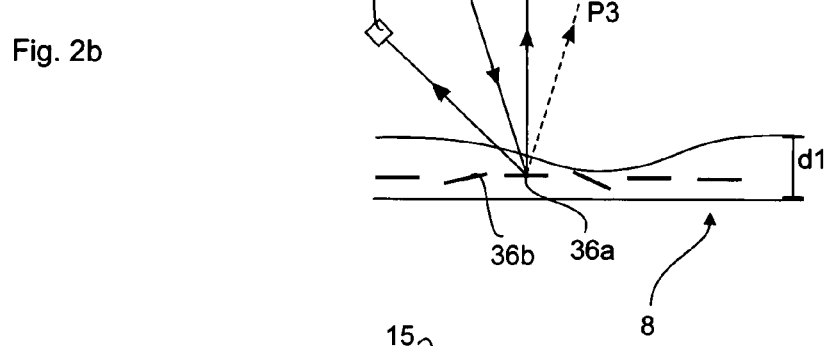
Figure 2C:
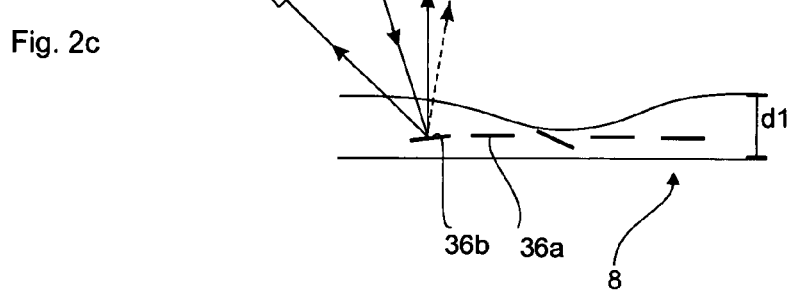

FIGS. 2a to 2c relate to a further problem on which the invention is based. Here, reference 8 denotes the surface or a corresponding coating. Within this coating, in some types of coating there is a large number of so-called pigments or flakes 36a, 36b. In the case of a proper coating, the flakes are oriented essentially horizontally, like the flake 36a for example. In the event of defects, however, oblique positions of the flakes may arise, as shown for example in the case of the flake 36b.

On the other hand, however, thickness fluctuations of the respective coating may arise, and these thickness fluctuations also have an effect on the optical impression of the surface and also on the measurement result. For example, in the region in which the coating is too thin and has a thickness d2, it is possible that a basecoat shows through and falsifies the overall impression. With the measurement method known from the prior art, it is not possible to determine from a recorded image or from a measurement that has been carried out whether fluctuations stem from a concentration fluctuation or from an incorrect orientation of the flakes.

Three different measurement situations are shown in FIGS. 2a to 2c. In said figures, reference 3 denotes a radiation device and references 15 and 7 denote radiation detector devices. The radiation device emits radiation onto the surface at an emission angle $\alpha 1$ of $-15°$ with respect to the median perpendicular M. This radiation is reflected at a reflection angle of 15° with respect to the median perpendicular M (arrow P3). The radiation detector device 15 receives a certain part of this reflected radiation, but the further radiation detector device 7 on the other hand receives only scattered radiation.

FIG. 2a shows a starting situation in which a measurement is carried out at the location of a correctly oriented flake 36a, wherein the layer thickness here has the value d1. FIG. 2b shows a situation in which, although the flake is correctly oriented, nevertheless the layer thickness has a reduced value d2. As mentioned above, changes in intensity may occur in this region on account of the reduced layer thickness or the colour pigment concentration.

However, this change in intensity will have the same effect on the radiation detector device 15, which is arranged at $-15°$ with respect to the direction of the reflected radiation, and on the radiation detector device 7, which is arranged at $-45°$ with respect to the direction of the reflected radiation. Layer thickness changes, which can also be referred to as clouds, therefore act on the respective signals in the same way or in the same direction.

FIG. 2c shows a situation in which the emitted light impinges on the flake 36b, which is rotated in terms of its orientation. However, the illustrated flake 36b also represents a large number of flakes. In this case, the rotation means that the reflected signal no longer impinges at 15°. This is illustrated by the arrow P3 shown in dashed line. In this case, therefore, the radiation detector device 15 will receive a higher proportion of the reflected light. By contrast, the intensity of the scattered light, which impinges on the radiation detector device 7, will not change significantly or will change in some other way. In this case, therefore, the intensity of the radiation which impinges on the second radiation detector device 15 and the radiation which impinges on the further detector device 7 thus change differently or in opposite directions. The cause of intensity changes can thus be determined by comparing the received intensities. With a large number of incorrectly oriented flakes, generally the intensity of the reflected light will decrease and the intensity of the scattered light will increase.

In other words, although such so-called orientation clouds (i.e. areas containing incorrectly oriented flakes) change the properties of colour changes, they nevertheless in each case have a different effect on the respectively measured signals, depending on the arrangement of the radiation detector device in the circumferential direction. In this case, too, the percentage deviation of the signals received in each case by the two radiation detector devices 7 and 15 is summed or compared, wherein this summing or comparison may take place over different ranges of length distances. In this way, the physical cause of colour changes can be ascertained and the types of colour changes can be distinguished from one another.

With reference to FIG. 1, it can be seen that thickness changes here too change the sensor signals at $-15°$ and $+15°$ in the same direction, and for example the total signal is increased. Here, too, the percentage deviation between the signals at $+15°$ and $-15°$ are summed. However, as already mentioned, tilting of the surface gives rise to opposite changes in the signals of the radiation detector devices. In this case, however, the sum of the two signals (which are received at $-15°$ and $+15°$ with respect to the direction of the reflected light) is essentially independent of the tilting of the apparatus with respect to the surface since, as mentioned, the arrangement of the radiation detector device is selected in such a way that the measurement is carried out in each case in the essentially linear region of the flanks of the signals 31 and 33.

Figure 3:
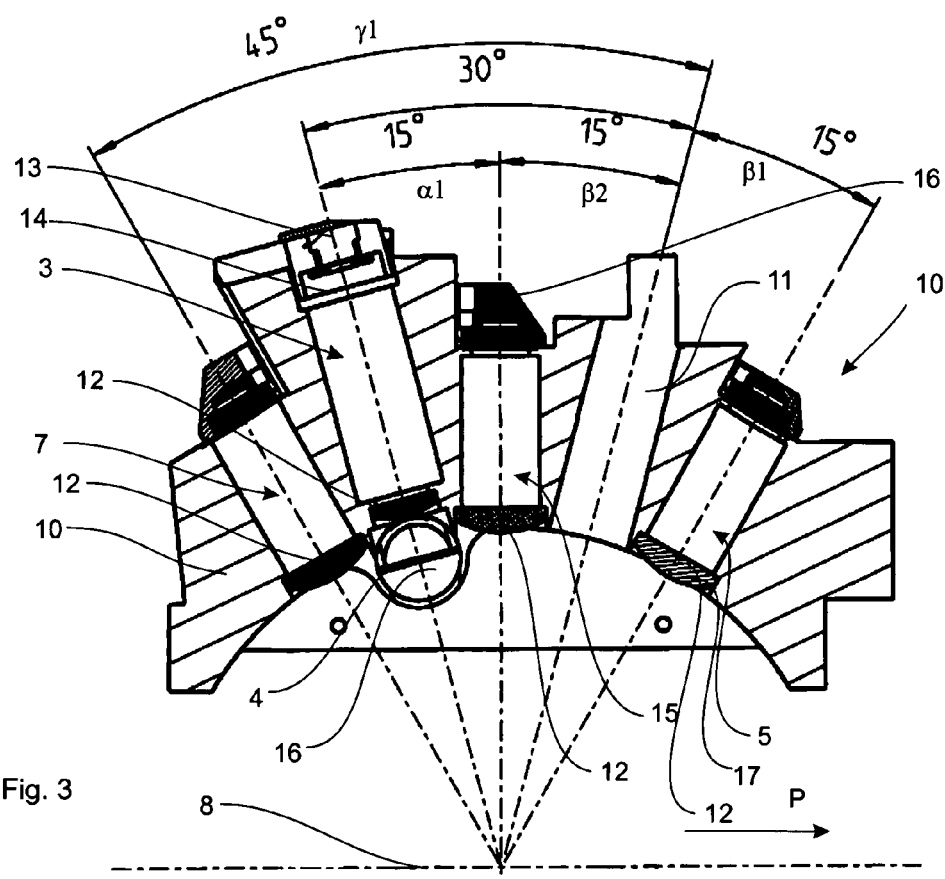
FIG. 3 shows an optical block of an apparatus according to the invention.

FIG. 3 shows an optical block 10 of an apparatus according to the invention for analysing surface properties. Here, reference 3 denotes a radiation detector device which emits radiation onto a surface 8 to be analyzed. During operation, the apparatus is moved along the arrow P with respect to the surface in order to optically scan the surface in this way.

In principle, it would also be possible to arrange a plurality of radiation devices parallel to one another, for example in a direction perpendicular to the plane of the figure. In addition, optical elements such as cylindrical lenses may also be provided, which cause radiation to be emitted onto the surface along a line perpendicular to the plane of the figure. In this way, it is possible to optically measure simultaneously not just linear elements but rather two-dimensional elements.

Reference 13 denotes a light source which may for example be a white LED. The radiation emitted by the LED passes through a diaphragm 14 and a lens 12 onto the surface 8. Here, the radiation device is arranged at an emission angle $\alpha 1$ of 15° with respect to the median perpendicular M. The reflected light is thus also reflected at an angle of 15° by the surface 8. Reference 11 denotes an absorption device which essentially absorbs the reflected radiation. This may be for example a tube or the like. The absorption device is preferably closed in order to prevent the entry of external light into the apparatus.

Reference 5 denotes a first radiation detector device which is arranged at an angle $\beta 1$ of $+15°$ with respect to the direction of the reflected light. In the present embodiment, the first radiation detector device 5 is thus arranged at an angle of 30° with respect to the median perpendicular M. A second radiation detector device 15 is arranged at an angle $\beta 2$ of $-15°$ with respect to the direction of the reflected radiation and in this case is located vertically above the surface 8. These two radiation detector devices 5, 15 have photocells, and preferably CCD chips, which also allow locally resolved analysis of the radiation. In addition, the two radiation detector devices have lenses 17 and also diaphragms (not shown in detail).

Reference 16 denotes an intensity measuring device which is provided next to the radiation device 3. By means of this intensity measuring device, part of the radiation is coupled out of the radiation device and, as mentioned above, is used to calibrate and stabilize the measurement results. This intensity measuring device 16 may likewise have optical elements (not shown) such as diaphragms, filters, photodiodes and the like.

Reference 7 denotes a further radiation detector device. This further radiation detector device 7 is arranged at an angle of $\gamma 1 = -45°$ with respect to the direction of the reflected radiation and therefore receives light scattered by the surface. This radiation detector device preferably also allows locally resolved reception of the radiation impinging thereon. As explained above, the physical cause of intensity fluctuations can be deduced from a comparison of the measurement signals received by one of the radiation detector devices 5 or 15 with the signal received by the radiation detector device 7.

However, besides the radiation detector devices shown, further radiation detector devices may also be provided, for example at large angles with respect to the median perpendicular, such as 70° or 80° for example. In addition, it would also be possible to provide further radiation devices and also filter elements which separate light of different spectral components from one another.

Figure 4:
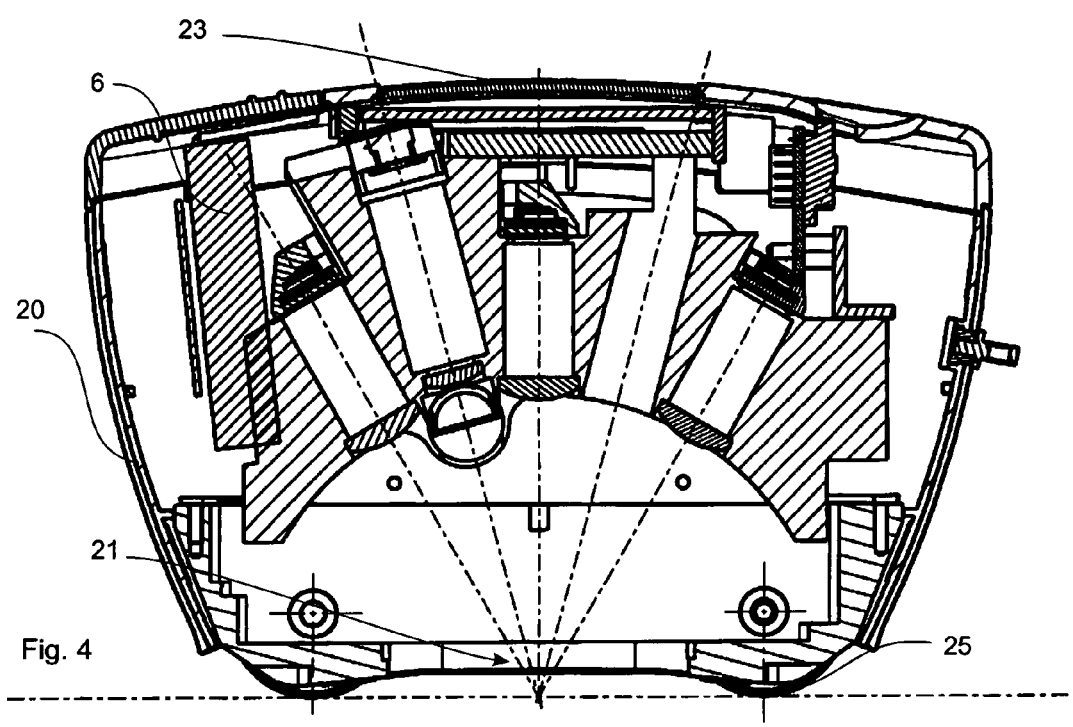
FIG. 4 shows an apparatus according to the invention.

FIG. 4 shows an apparatus 1 according to the invention with the optical unit 10 shown in FIG. 3. In addition, the apparatus has a housing 20 in which the aforementioned optical unit 10 is installed. Reference 21 denotes an opening in the lower housing region, through which the radiation passes from the radiation device 3 onto the surface 8. Reference 25 denotes a wheel of the apparatus for moving the apparatus with respect to the surface. Preferably, this wheel or else a different wheel is coupled to a distance measuring device in order to determine a distance traveled by the apparatus 1 with respect to the surface. Reference 23 denotes a display device such as a screen. Reference 6 denotes a processor device which compares the individual measurement signals with one another.

By the cooperation between the distance measuring device and the individual radiation detector devices, a profile of the determined data can be recorded over the surface and a distance/time profile can be determined.

Figure 5A:
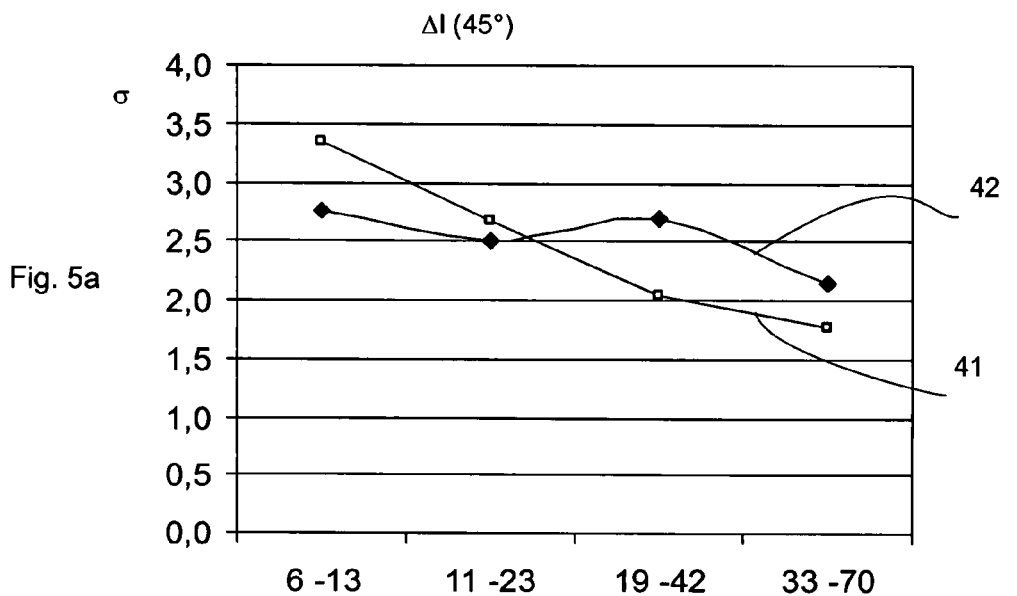
FIG. 5a shows a first diagram to illustrate measurement results.
Figure 5B:
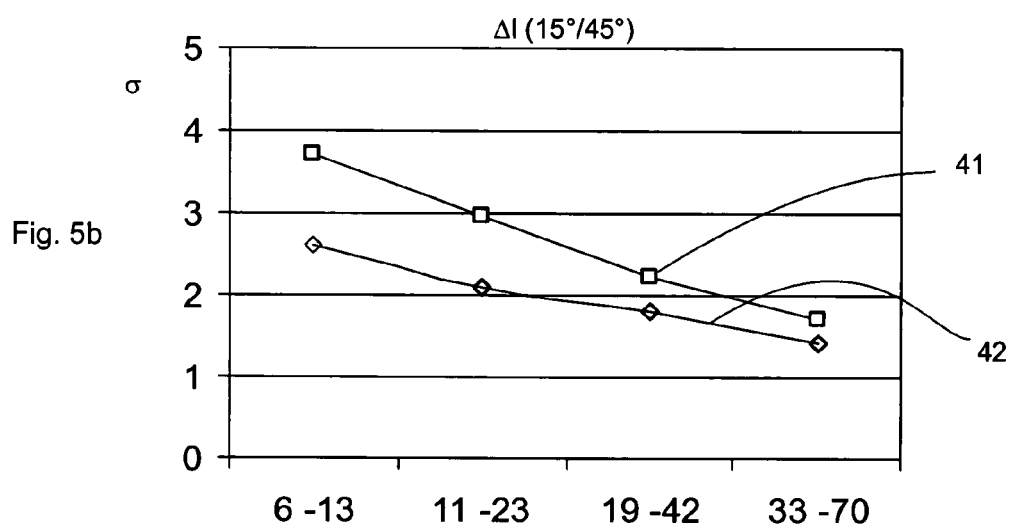
FIG. 5b shows a second diagram to illustrate measurement results.
Figure 5C:
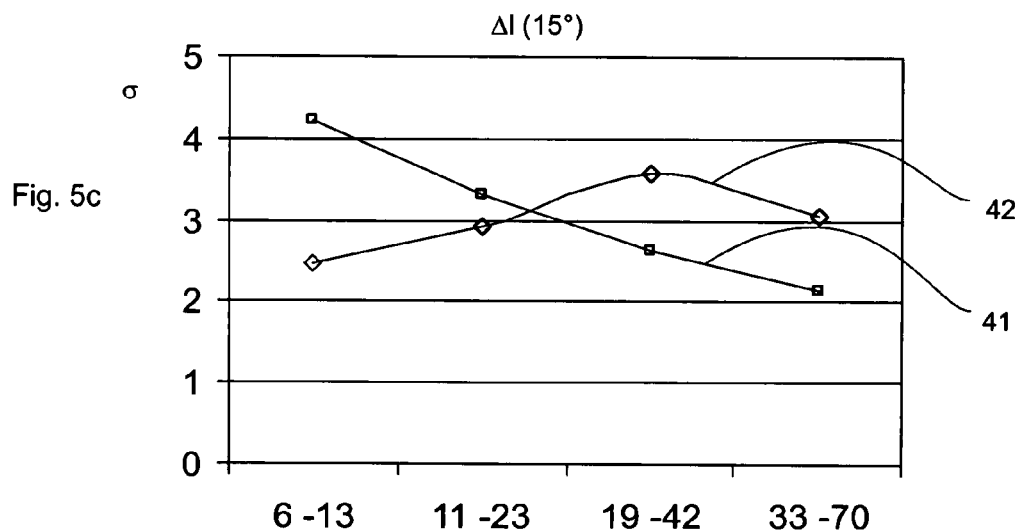
FIG. 5c shows a third diagram to illustrate measurement results.

FIGS. 5a, 5b and 5c show spectra recorded by the apparatus according to the invention. Here, reference 41 denotes a spectrum which was recorded from a reference surface, and reference 42 denotes a spectrum which was recorded with a further surface to be analyzed. The standard deviation $\sigma$ of the determined intensities is plotted on the Y coordinate in each case. For each surface, a total of four measured values were recorded, with different spatial regions (hereinafter also referred to as spatial wavelengths) in millimeters being plotted on the coordinate.

More specifically, this means that averaging was carried out over distances between 6 and 13 millimeters in the first region, averaging was carried out in a distance range between 11 and 23 millimeters in the second region, averaging was carried out over distances in a range from 19 to 42 millimeters in the third region, and averaging was carried out in a distance range between 33 and 70 millimeters in the fourth region. These different distances represent the distance of an observer from the respective surface, for example a motor vehicle paintwork. The third region with distances from 19 to 42 millimeters thus corresponds to a viewing distance of between 2 and 3 meters.

FIG. 5a shows the light intensity changes which were recorded by the radiation detector device arranged at 45°. Here, a surface was selected which had thickness changes in its base coating. FIG. 5c shows a corresponding diagram for the radiation received at 15°, i.e. for example by the radiation detector device 5. As can be seen by comparing FIGS. 5a and 5c, due to the change in layer thickness the signals of both radiation detector devices change in the same way here, i.e. they both have a maximum in the region of 19 to 42 millimeters.

FIG. 5b shows a comparison of the intensities recorded by the two radiation detector devices at 15° and 45°. Here too, like in the two other graphs, the signals of the two radiation detector devices arranged at +15° and −15° with respect to the direction of the reflected light were averaged or summed. It can be seen from FIG. 5b that the difference or ratio of the two intensities has a relatively small standard deviation which, as mentioned above, makes it possible to deduce that the surface has a uniform orientation of the flakes but is subject to certain thickness fluctuations.

In the case of effects brought about by a non-uniform orientation of the flakes, the standard deviation would accordingly assume higher values.

Preferably, therefore, an apparatus is provided which comprises both a first and a second and also a further radiation detector device. In this way, different causes of measurement deviations can be determined in a particularly simple manner, be these caused by tilting of the apparatus with respect to the surface, by a changing orientation of the flakes or by a change in layer thickness.

All the features disclosed in the application documents are claimed as essential to the invention in so far as they are novel individually or in combination with respect to the prior art.

| List of references | |
|---|---|
| 1 | apparatus |
| 3 | radiation device |
| 5 | first radiation detector device |
| 6 | processor device |
| 7 | further radiation detector device |
| 8 | surface |
| 10 | optical block |
| 11 | absorption device |
| 12 | lens |
| 13 | light source |
| 14 | diaphragm |
| 15 | second radiation detector device |
| 16 | intensity measuring device |
| 17 | lens |
| 20 | housing |
| 21 | opening in the lower housing region |
| 23 | display device |
| 25 | wheel of the apparatus |
| 31, 33 | signals |
| 36a, 36b | flake (pigment) |
| 41, 42 | spectrum |
| $I_0, I_1, I_2$ | intensity |
| P, P3 | arrow |
| $d_1, d_2$ | layer thicknesses |
| $\alpha_1$ | emission angle |
| $\beta 1, \beta 2, \gamma 1$ | angles of the radiation detector devices |
| M | median perpendicular |

The invention claimed is:

1. An apparatus for determining surface properties, comprising:
   at least a first radiation device which emits radiation onto a surface to be analyzed;
   at least a first radiation detector device which receives at least part of the radiation emitted by the at least one radiation device and then scattered by the surface and outputs at least a first measurement signal which is characteristic of the scattered radiation;

at least one second radiation detector device which receives at least part of the radiation emitted by the at least one radiation device and then scattered by the surface and outputs at least a second measurement signal which is characteristic of the scattered radiation;

an absorption device for absorbing the radiation reflected by the surface; and a processor device that takes into account the position of the apparatus with respect to the surface from a relation between the first measurement signal and the second measurement signal, wherein the first radiation detector device is offset by a first predefined angle β1 with respect to the direction of the radiation reflected by the surface, the second radiation detector device is offset by a further predefined angle β2 with respect to the direction of the radiation reflected by the surface, the angles β1 and β2 are essentially equal and opposite to one another with respect to the direction of the radiation reflected by the surface, and both the radiation device and the first radiation detector device and the second radiation detector device are all arranged in the same plane of an observed beam path, and wherein the absorption device is arranged at the reflection angle of the reflected radiation with respect to the surface.

2. The apparatus according to claim 1, wherein the relation is a difference or a ratio.

3. The apparatus according to claim 1, wherein the value of the predefined angles β1 and β2 is between 5° and 35°, preferably between 10° and 30°, more preferably between 15° and 25°, and especially preferably about 15°.

4. The apparatus according to claim 1, wherein the first radiation device emits radiation at a predefined angle α1 onto the surface and this angle α1 is between 5° and 45°, preferably between 10° and 35°, more preferably between 10° and 25°, and especially preferably about 15° with respect to a direction perpendicular to the surface.

5. The apparatus according to claim 1, comprising a further radiation detector device which receives at least part of the radiation emitted by the at least one radiation device and then scattered by the surface and outputs at least a further measurement signal which is characteristic of the scattered radiation.

6. The apparatus according to claim 5, wherein the further radiation detector device is arranged under a further angle with respect to a direction perpendicular to the surface wherein this angle has a value between 30° and 60° and preferably of about 45°.

7. The apparatus according to claim 5, comprising a processor device which compares the further measurement signal with at least one of the first or the second measurement signals and outputs a value characteristic of this comparison.

8. An apparatus for determining surface properties, comprising:

at least a first radiation device which emits radiation onto a surface to be analyzed;

at least a first radiation detector device which receives at least part of the radiation emitted by the at least one radiation device and then scattered by the surface and outputs at least a first measurement signal which is characteristic of the scattered radiation;

at least a further radiation detector device which receives at least part of the radiation emitted by the at least one radiation device and then scattered by the surface and outputs at least a second measurement signal which is characteristic of the scattered radiation;

an absorption device for absorbing the radiation reflected by the surface; and a processor device that determines a value characteristic for a surface quality from a relation between the first measurement signal and the second measurement signal and that takes into account the position of the apparatus with respect to the surface from a relation between the first measurement signal and the second measurement signal, wherein the first radiation detector device is offset by a first predefined angle β1 with respect to the direction of the radiation reflected by the surface, the further radiation detector device is offset by a further predefined angle γ1 with respect to the radiation reflected by the surface, wherein the first radiation device, the first radiation detector device and the further radiation detector device are all arranged in the same plane of an observed beam path, and wherein the first predefined angle β1 and the further predefined angle γ1 differ from each other, and the absorption device is arranged at the reflection angle of the reflected radiation with respect to the surface.

9. The apparatus according to claim 1, comprising an intensity measuring device which measures the intensity of the radiation emitted by the radiation device before said radiation impinges on the surface.

10. The apparatus according to claim 1, wherein at least one radiation detector device allows locally resolved reception of the radiation impinging thereon.

11. A method for determining surface properties, comprising the following steps:

emitting radiation with a radiation device onto a surface to be analyzed;

absorbing reflected radiation, using an absorption device arranged at the reflection angle of the reflected radiation with respect to the surface;

detecting, using a first radiation detector device which is arranged in the same plane as the radiation device and an observed beam path, at least part of the radiation emitted onto the surface and scattered by the latter and outputting a first signal characteristic of this scattered radiation;

detecting, using a second radiation detector device which is arranged in the same plane as the radiation device and the observed beam path, at least part of the radiation emitted onto the surface and scattered by the latter and outputting a second signal characteristic of this scattered radiation, wherein radiation device, the first radiation detector device and the second radiation detector device are all arranged on the same plane of the observed beam path;

comparing the first signal with the second signal; and taking into account a geometrical position of the radiation device with respect to the surface by taking as a basis the comparison between the first measurement signal and the second measurement signal.

12. A method for determining surface properties, comprising the following steps:

emitting radiation onto a surface to be analyzed using an radiation emitting device;

absorbing reflected radiation, using an absorption device arranged at the reflection angle of the reflected radiation with respect to the surface;

detecting, using a first radiation detector device, at least part of the radiation emitted onto the surface and scattered by the latter and outputting a first signal characteristic of this scattered radiation;

detecting, using a further radiation detector device, at least part of the radiation emitted onto the surface and scattered by the latter and outputting a further signal characteristic of this scattered radiation, wherein the radiation emitting device, the first radiation detector device, and the further radiation detector device are all arranged in the same plane of an observed beam path;

comparing the first signal with the further signal and outputting a value characteristic of this comparison: and taking into account the position of the apparatus with respect to the surface from a relation between the first measurement signal and the second measurement signal.

13. The apparatus according to claim 8, wherein an intensity measuring device is provided which measures the intensity of the radiation emitted by the radiation device before said radiation impinges on the surface.

14. The apparatus according to claim 8, wherein at least one radiation detector device allows locally resolved reception of the radiation impinging thereon.

* * * * *